United States Patent

Oude Alink et al.

[11] 4,174,370
[45] Nov. 13, 1979

[54] SUBSTITUTED PYRIDINES

[75] Inventors: Bernardus A. Oude Alink, St. Louis; Neil E. S. Thompson, Creve Coeur, both of Mo.

[73] Assignee: Petrolite Corporation, St. Louis, Mo.

[21] Appl. No.: 937,040

[22] Filed: Aug. 25, 1978

Related U.S. Application Data

[62] Division of Ser. No. 604,609, Aug. 14, 1975.

[51] Int. Cl.$^2$ .................................................. C23F 9/00
[52] U.S. Cl. .................................. 422/12; 252/8.55 E; 252/390; 252/180; 106/14.13; 422/16; 422/17
[58] Field of Search .................... 252/390, 8.55 E, 180; 422/15, 16, 17; 260/290, 295, 294.8, 256.4, 295 S, 290 P; 106/14.13; 210/59

[56] References Cited

U.S. PATENT DOCUMENTS

| | | | |
|---|---|---|---|
| 2,501,209 | 3/1950 | Craig | 260/290 |
| 4,003,718 | 1/1977 | Gattuso | 252/390 |
| 4,022,785 | 5/1977 | Alink et al. | 252/390 |
| 4,071,746 | 1/1978 | Quinlan | 252/390 |

*Primary Examiner*—Benjamin R. Padgett
*Assistant Examiner*—J. L. Barr

*Attorney, Agent, or Firm*—Sidney B. Ring; Hyman F. Glass

[57] ABSTRACT

This invention relates to substituted pyridines prepared by reacting aldehydes, amines, lower carboxylic acids such as acetic acid in the presence of oxygen. The N-substituted pyridinium salts formed can be converted to pyridines by thermal dealkylation.

The reactions can be summarized by the following equations:

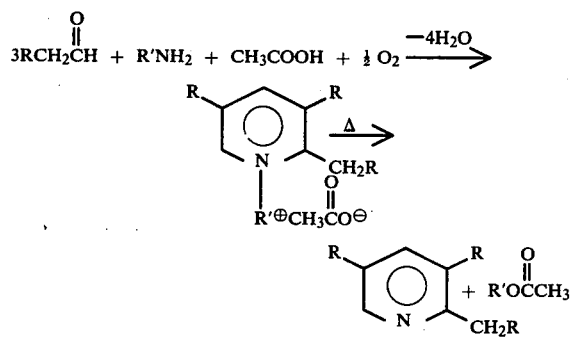

4 Claims, No Drawings

SUBSTITUTED PYRIDINES

This is a division of application Ser. No. 604,609, filed Aug. 14, 1975.

We have discovered novel substituted pyridines and a method for their preparation which comprises reacting an aldehyde, an amine, a carboxylic acid and oxygen. The overall reaction may be summarized as follows:

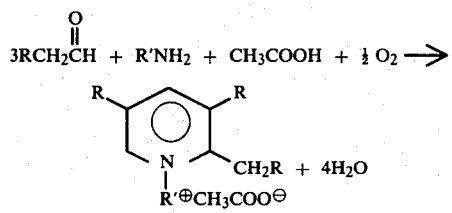

It is believed that the reaction takes place in two steps.

Step 1 involves the formation of a dihydropyridine according to the following reaction:

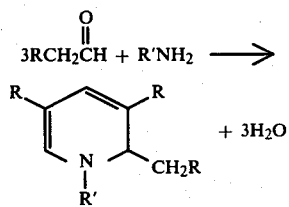

Step 2 involves the oxidation of the dihydropyridine with oxygen containing gas in the presence of acetic acid according to the following equation:

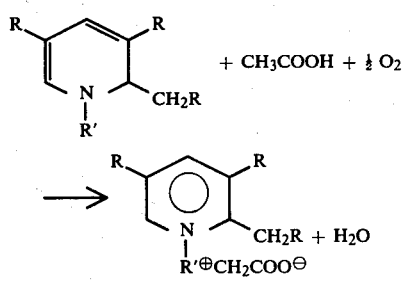

Acetic acid acts as a catalyst in both steps, i.e., in both the formation of and in the oxidation of the dihydropyridine.

We have also discovered that pyridinium acetates formed can be converted to the corresponding pyridines in excellent yield by the thermal dealkylation according to the following equation:

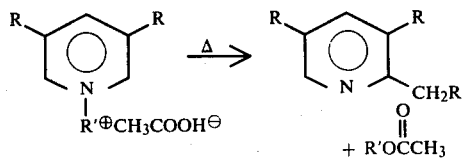

Any suitable aldehyde can be employed, i.e., any aldehyde having a

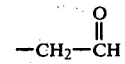

group except acetaldehyde. This includes aldehydes of the formula

where R is alkyl, aryl, cycloalkyl, alkaryl, aralkyl, heterocyclic, etc. R is preferably alkyl, for example having from 1 to 30 or more carbons, such as from 1 to 18 carbons but preferably from 1–12 carbons. These include for example proprionaldehyde, butyraldehyde, heptaldehyde, etc., as well as substituted aldehydes such as aldol, etc.

Also included are polyaldehydes such as those of the general formula

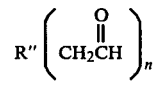

where R'' is alkylene, cycloalkylene, arylene, heterocyclic, etc., for example of the general formula

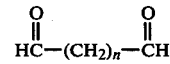

where n=1–18 or more, for example succinaldehyde, etc.

Also included are arylpolyaldehydes such as those of the general formula

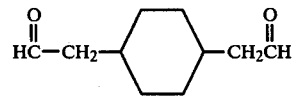

or isomers or substituted derivatives thereof, etc.

Any suitable primary amine can be employed. These include compounds of the formula $R'-NH_2$, where R' is a substituted group preferably a hydrocarbon group, for example alkyl, cycloalkyl, aryl, alkenyl, heterocyclic, substituted derivatives of the above, etc.

ALKYL

Alkyl includes methyl, ethyl, propyl, butyl, amyl, hexyl, heptyl, octyl, nonyl, decyl, undecyl, dodecyl, tridecyl, tetradecyl, pentadecyl, hexadecyl, heptadecyl, octadecyl, eicosyl, docosyl, etc. having 1–50 or more carbons, such as 1–30, but preferably 12–18 carbons.

The term "alkyl" also includes isomers of the straight chain group wherein branching occurs along the chain, for example

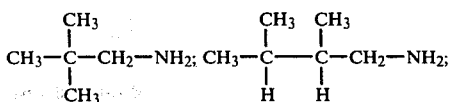

-continued

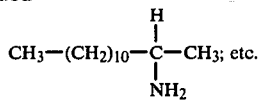

ALKENYL AND ALKINYL

These include unsaturated analogues (for example, 2-50, such as 2-30 carbon atoms) of alkyl groups containing one or more —C=C— or —C≡C— groups, for example, decenyl, dodecenyl, tridecenyl, tetradecenyl, pentadecenyl, hexadecenyl, heptadecenyl, octadecentyl, etc., dienes for example octadienyl, etc., trienes, for example octatrienyl, etc., alkinyl, for example, butinyl, etc.

CYCLOALKYL

These include:

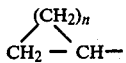

for example cyclobutyl, cyclopentyl, cyclohexyl, cycloheptyl, cyclooctyl, etc.; substituted derivatives thereof, for example alkyl or polyalkyl, for example alkyl cyclohexyl, dialkyl cyclohexyl, etc.

ARYL

These include phenyl, substituted phenyl, alkylphenyl, polyalkylphenyl, chlorophenyl, alkoxyphenyl, etc., naphthyl, alkyl naphthyl, etc.; benzyl substituted benzyl, etc., groups.

HETEROCYCLIC

These include furyl, pyranyl, hydrogenated furyl, pyranyl, etc., groups.

The following are examples of commercial amines. The nomenclature of such amines is derived from either their chain length or source of raw materials, for example, Armeen 8D—Octyl amine
Armeen C—Coconut oil amine
Armeen S—Soybean oil amine
Armeen T—Tallow amine
Armeen O—Oleyl amine
Armeen HT—Hydrogenated tallow amine Products with "D" designate distilled grade. Products without "D" designate technical grade.

The polyamines employed in this invention include those of the following formula:

$$NH_2(AN)_nH$$

where n is for example 1-8 or greater, where A is a divalent radical for example straight chained or branched —(CH$_2$)$_m$, —CH$_2$—CH$_2$—,

and m is for example 2-10 or greater. These include the following:

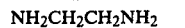
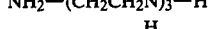
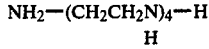
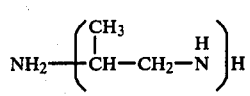
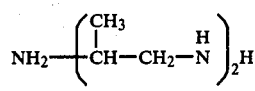
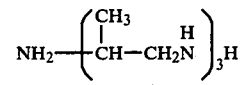
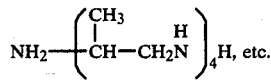
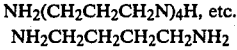
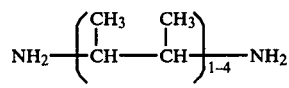
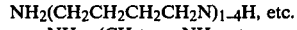
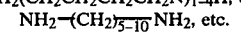

Other examples include the following alkylated polyamines for example of the formula

where the R'''s are H or a substituted group, such as alkyl, alkenyl, alkinyl, aryl, etc. The preferable type is of the formula

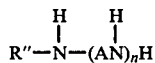

(R is straight chained or branched)
Examples include the following:

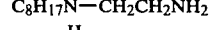
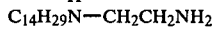
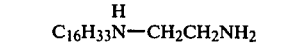

-continued

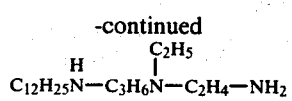

Other suitable amines are exemplified by:

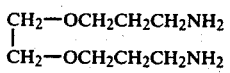

Preacylated amines can also be employed provided the resulting amino amide has at least two labile-nonamido hydrogens, for example

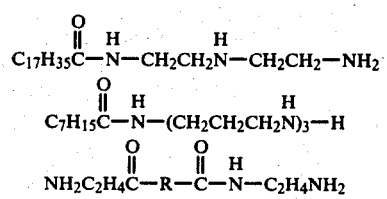

Aromatic polyamines can also be employed, for example:

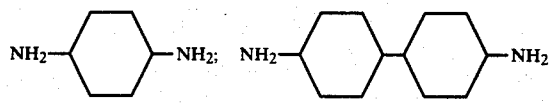

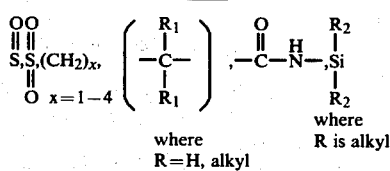

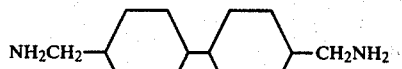

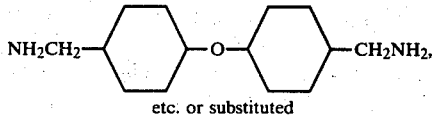

etc. or substituted

Also included are substituted amines, for example hydroxylamines, such as hydroxyalkyl amines, having 2-10 or more carbons,
  monoethanol amine
  monoisopropanol amine
  monopentanol amine
  monohexanol amine
  2-amino-2-methyl-1-propanol
  2-amino-2-methyl-1,3-propanediol
  2-amino-2-ethyl-1,3-propanediol
  3-amino-2-methyl-1-propanol
  2-amino-1-butanol
  3-amino-2,2-dimethyl-1-propanol
  2-amino-2,3-dimethyl-1-propanol
  2,2-diethyl-2-amino ethanol
  2,2-dimethyl-2-amino ethanol
  3-amino-1,2-butanediol
  4-amino-1,2-butanediol
  2-amino-1,3-butanediol
  4-amino-1,3-butanediol
  2-amino-1,4-butanediol
  3-amino-1,4-butanediol
  1-amino-2,3-butanediol, etc.

Also included are heterocyclic amines, such as furfurylamine, cyclic amidines, etc.

Cyclic amidines are derived conveniently from carboxy acids, including polycarboxy acids. As is well known, some polycarboxy acids have 3 or more carboxyl radicals; thus, it is possible to obtain cyclic amidines in which 3 or more ring radicals appear.

Cyclic amidines, such as imidazolines and tetrahydropyrimidines, having an amino side chain can be reacted, for example

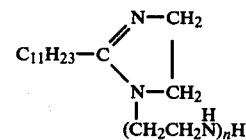

1-polyethylene amine, 2-undecylimidazoline

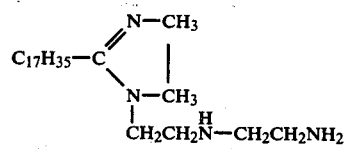

1-diethylene diamine, 2-heptadecylimidazoline

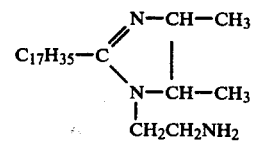

1-amino ethyl, 2-heptadecyl-4,5-dimethylimidazoline

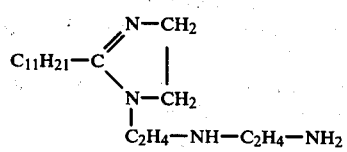

1-diethylenediamine, 2-undecyleneylimidazoline

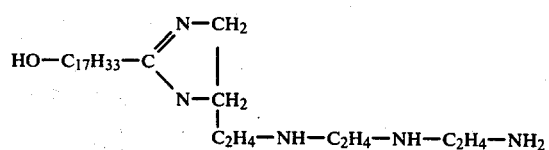

1-triethylenetriamine, 2-hydroxyheptadecyleneylimidazoline

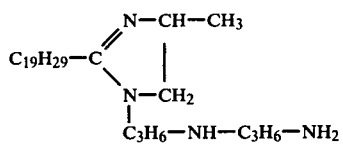

1-aminopropylaminopropyl, 2-abietyl, 4-methylimidazoline

Tetrahydropyrimidines from monocarboxy acids and trimethylenepolyamines.

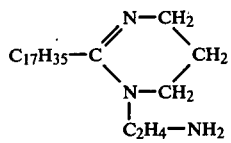

1-aminoethyl, 2-heptadecyltetrahydropyrimidine

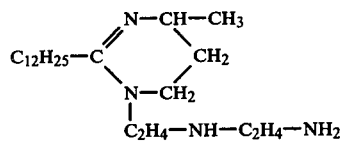

1-aminoethylaminoethyl, 2-dodecyl, 4-methyl tetrahydropyrimidine

Any suitable carboxylic acid can be employed for example the aliphatic carboxylic acids such as

RCOH, where R is alkyl, for example having 1-9 carbons, such as 1-6 carbons, but preferably acetic acid.

The reaction is carried out at any suitable temperature up to decomposition temperature of reactants and product. In general, the reaction is carried out from room temperature to about 150° C., but preferably from about 60°-110° C. The oxidation reaction can be carried out at ambient temperature whereas the dihydropyridine reaction is preferably carried out at 60° C. or higher. Where the reaction is carried out as a one step process temperatures of about 60°-110° C. are generally employed. The reaction is carried out until the desired product is obtained such as from about 1-18 hrs., for example from 3-12 hours, but preferably from about 3 to 8 hours.

The following examples are presented for purposes of illustration and not of limitation.

EXAMPLE 1

1-Methyl-2-propyl-3,5-diethyl pyridinium acetate

In a pressure reactor was placed 250.6 grams of butyraldehyde and 69.7 grams of acetic acid. To the mixture was added over a 5 minute period, 38.5 grams of methylamine, while a reaction temperature of 67°-75° C. was maintained. Oxygen gas was added to 40-70 psi and the mixture stirred for 8 hours. The reaction mixture was cooled to ambient temperature and 150 grams of water was added. The aqueous phase was extracted with ether, and evaporated under diminished pressure to yield 246 grams of 1-methyl-2-propyl-3,5-diethyl-pyridinium acetate, n.m.r., solvent $D_2O$, δ in pm, 8.68 m, 1H; 8.52 m, 1H; 4.48, s, 3H; 3.00 m, 6H; 2.12, s, 3H, 1.78 m, 2H; 1.37 and 1.17 t's, 9H.

EXAMPLE 2

1-Methyl-2-propyl-3,5-diethyl 1,2-dihydropyridine

In a pressure reactor was charged 303 g of butyraldehyde and 6 g of acetic acid. To the mixture was added with stirring 49.8 grams of methylamine at such a rate that a temperature of 95°-100° C. was reached. The reaction mixture was stirred for 5 hrs. at 95°-100° C. The two layers produced were separated and the aqueous phase extracted with ether. The ethereal solution was combined with the organic layer. The aqueous phase upon evaporation yielded 26.8 grams of 1-methyl-2-propyl-3,5-diethyl pyridinium acetate identical to the product described in example 1. The ethereal solution upon evaporation yielded 254.3 grams of product. Distillation yielded a fraction, 31.2 g, b. 150°-215° C., identified as a mixture of 2-ethylhexenal and the imine of 2-ethylhexenal, the fraction 218.2 g b. 227°-235° C. was identified as 1-methyl-2-propyl-3,5-diethyl 1,2-dihydropyridine, n.m.r. (solvent benzene $d_6$), δ in ppm, 5.63, m, 1H; 5.51, m, 1H; 3.57 m, 1H; 2.57, s, 3H; 2.03 m, 4H; 1.42 m, 4H; 1.03 and 0.95, t's, 9H.

Anal. calcd. for $C_{13}H_{23}N$: N, 7.25; Found: N, 7.02.

EXAMPLE 3

1-Methyl-2-propyl-3,5-diethyl pyridinium acetate

A sample of 38.6 g of 1-methyl-2-propyl-3,5-diethyl 1,2-dihydropyridine was added to a mixture of 12 grams of acetic acid and 26 grams of water. The mixture was stirred and air was introduced for 18 hours. The resulting aqueous phase was evaporated under diminished pressure to yield 48.2 grams of 1-methyl-2-propyl-3,5diethylpyridinium acetate, identical to the product described in example 1.

EXAMPLE 4

2-Propyl-3,5-diethylpyridine

A mixture of 216.2 g of butyraldehyde and 65 g of acetic acid was placed in a pressure reactor. To the mixture was added 30.4 g of methylamine. The reaction temperature was adjusted to 75°-80° C. and oxygen gas was added over a 5 hour period at 40-70 psi while the reaction mixture was stirred. The product was cooled to ambient temperature and dissolved in 257 g of water. The aqueous solution was evaporated under diminished pressure to yield 243.3 g of product. The resulting product was slowly distilled at atmospheric pressure and the distillate, boiling point to 250° C. was collected as 214.8 grams of a 1:1 molar mixture of methylacetate and 2-propyl-3,5-diethylpyridine. After removal of the methylacetate under diminished pressure, there was obtained 152.3 g of 2-propyl3,5-diethylpyridine; n.m.r. (solvent $CDCl_3$) δ in ppm, 8.19, d, 1H; 7.22, d, 1H; 2.64 m, 6H; 1.68, m, 2H; 1.18 and 0.98, t's, 9H Anal. calced. for $C_{12}H_{19}N$, N, 7.91;
Found, N, 7.87.

As described in example 1, the following pyridinium acetate salts were synthesized from an aldehyde, an amine, acetic acid and oxygen gas. The results are collected in Table I.

Table I.

| Example No. | Aldehyde | Amine | Reaction Product |
|---|---|---|---|
| 5 | Propionaldehyde | Methylamine | 1,3,5-trimethyl-2-ethyl pyridinium acetate |
| 6 | Propionaldehyde | Butylamine | 1-butyl-2-ethyl-3,5-dimethyl pyridinium acetate |
| 7 | Butyraldehyde | Ethylamine | 1,3,5-triethyl-2-propyl pyridinium acetate |
| 8 | Butyraldehyde | Propylamine | 1,2-dipropyl-3,5-diethyl pyridinium acetate |
| 9 | Butyraldehyde | Butylamine | 1-butyl-2-propyl-3,5-diethyl pyridinium acetate |
| 10 | Butyraldehyde | Monoethanol-amine | 1-ethylhydroxy-2-propyl-3,5-diethylpyridinium acetate |
| 11 | Butyraldehyde | Aniline | 1-phenyl-2-butyl-3,5-diethyl pyridinium acetate |
| 12 | Butyraldehyde | Dodecylamine | 1-dodecyl-2-butyl-3,5-diethyl pyridinium acetate |
| 13 | Valeraldehyde | Methylamine | 1-meyhyl-2-pentyl-3,5-dibutylpyridinium acetate |
| 14 | Valeraldehyde | Pentylamine | 1,2-dipentyl-3,5-dibutyl pyridinium acetate |
| 15 | Nonylaldehyde | Methylamine | 1-methyl-2-octyl-3,5-diheptyl pyridinium acetate |

Where polyamines or polyaldehydes are employed instead of monoamines and monoaldehydes, the products are of the same general structure, but are monocyclic, polycyclic, polymeric or mixtures thereof.

USE AS CORROSION INHIBITORS

This phase of this invention relates to the use of these compounds in inhibiting the corrosion of metals, most particularly iron, steel and ferrous alloys. These compounds can be used in a wide variety of applications and systems where iron, steel and ferrous alloys are affected by corrosion. They may be employed for inhibiting corrosion in processes which require a protective or passivating coating as by dissolution in the medium which comes in contact with the metal. They can be used in preventing atmospheric corrosion, underwater corrosion, corrosion in steam and hot water systems, corrosion in chemical industries, underground corrosion, etc.

The corrosion inhibitors contemplated herein find special utility in the prevention of corrosion of pipe or equipment which is on contact with a corrosive oil-containing medium, as, for example, in oil wells producing corrosive oil or oil-brine mixtures, in refineries, and the like. These inhibitors may, however, be used in other systems or applications. They appear to possess properties which impart to metals resistance to attack by a variety of corrosive agents, such as brines, weak inorganic acids, organic acids, $CO_2$, $H_2S$, air or oxygen, etc.

The method of carrying out this process is relatively simple in principle. The corrosion preventive reagent is dissolved in the liquid corrosive medium in small amounts and is thus kept in contact with the metal surface to be protected. Alternatively, the corrosion inhibitor may be applied first to the metal surface, either as is, or as a solution in some carrier liquid or paste. Continuous application, as in the corrosive solution, is the preferred method, however.

The present process finds particular utility in the protection of metal equipment of oil and gas wells, especially those containing or producing an acidic constituent such as $H_2S$, $CO_2$, air or oxygen, organic acids and the like. For the protection of such wells, the reagent, either undiluted or dissolved in a suitable solvent, is fed down the annulus of the well between the casing and producing tubing where it becomes commingled with the fluid in the well and is pumped or flowed from the well with these fluids, thus contacting the inner wall of the casing, the outer and inner wall of tubing, and the inner surface of all wellhead fittings, connections and flow lines handling the corrosive fluid.

Where the inhibitor composition is a liquid, it is conventionally fed into the well annulus by means of a motor driven chemical injector pump, or it may be dumped periodically (e.g., once every day or two) into the annulus by means of a so-called "boll weevil" device or similar arrangement. Where the inhibitor is a solid, it may be dropped into the well as a solid lump or stock, it may be blown in as a powder with gas, or it may be washed in with a small stream of the well fluids or other liquid. Where there is gas pressure on the casing, it is necessary of course, to employ any of these treating methods through a pressure equalizing chamber equipped to allow introduction of reagent into the chamber, equalization of pressure between chamber and casing, and travel of reagent from chamber to well casing.

Occasionally, oil and gas wells are completed in such a manner that there is no opening between the annulus and the bottom of the tubing or pump. This results, for example, when the tubing is surrounded at some point by a packing held by the casing or earth formation below the casing. In such wells the reagent may be introduced into the tubing through a pressure equalizing vessel, after stopping the flow of fluids. After being so treated, the well should be left closed in for a period of time sufficient to permit the reagent to drop to the bottom of the well.

For injection into the well annulus, the corrosion inhibitor is usually employed as a solution in a suitable solvent. The selection of solvent will depend much upon the specific reagent being used and its solubility characteristics.

For treating wells with packed-off tubing, the use of solid "sticks" or plugs of inhibitor is especially convenient. These may be prepared by blending the inhibitor with a mineral wax, asphalt or resin in a proportion sufficient to give a moderately hard and high-melting solid which can be handled and fed into the well conveniently.

The protective action of the herein described reagents appears to be maintained for an appreciable time after treatment ceases, but eventually is lost unless another application is made.

For example, for the protection of gas wells and gas-condensate wells, the amount of corrosion inhibitor used might range between about ¼ to 3 lbs. per million cubic feet of gas produced, depending upon the amounts and composition of corrosive agents in the gas and the amount of liquid hydrocarbon and water produced. However, on no case does the amount of inhibitor required appear to be stoichiometrically related to the amount of acids produced by a well, since protection is obtained with much less corrosion inhibitor than usually would be required for neutralization of the acids produced.

These compounds are particularly effective in the prevention of corrosion in systems containing a corrosive aqueous medium, and most particularly in system containing brines.

These reagents can also be used in the prevention of corrosion in the secondary recovery of petroleum by water flooding and in the disposal of waste water and brine from oil and gas wells. Still more particularly, they can be used in a process of preventing corrosion in water flooding and in the disposal of waste water and bring from oil and gas wells which is characterized by injecting into an underground formation an aqueous solution containing minor amounts of the compositions of this invention, in sufficient amounts to prevent the corrosion of metals employed in such operation.

When an oil well ceases to flow by the natural pressure in the formation and/or substantial quantities of oil can no longer be obtained by the usual pumping methods, various processes are sometimes used for the treatment of the oil-bearing formation in order to increase the flow of oil. These processes are usually described as secondary recovery processes. One such process which is used quite frequently is the water flooding process wherein water is pumped under pressure into what is called an "injection well" and oil, along with quantities of water, that have been displaced from the formation, are pumped out of an adjacent well usually referred to as a "producing well." The oil which is pumped from the producing well is then separated from the water that has been pumped from the producing well and the water is pumped to a storage reservoir from which it can again be pumped into the injection well. Supplementary water from other sources may also be used in conjunction with the produced water. When the storage reservoir is open to the atmosphere and the oil is subject to aeration this type of water flooding system is referred to herein as an "open water flooding system." If the water is recirculated in a closed system without substantial aeration, the secondary recovery method is referred to herein as a "closed water flooding system."

Because of the corrosive nature of oil field brines, to economically produce oil by water flooding, it is necessary to prevent or reduce corrosion since corrosion increases the cost thereof by making it necessary to repair and replace such equipment at frequent intervals.

We have discovered a method of preventing corrosion in systems containing a corrosive aqueous media, and most particularly in systems containing brines, which is characterized by employing the compounds described herein. For example, we have discovered an improved process of protecting from corrosion metallic equipment employed in secondary oil recovery by water flooding such as injection wells, transmission lines, filters, meters, storage tanks, and other metallic implements employed therein and particularly those containing iron, steel, and ferrous alloys, such process being characterized by employing in water flood operation an aqueous solution of the compositions of this invention.

The invention, then, is particularly concerned with preventing corrosion in a water flooding process characterized by the flooding medium, containing an aqueous or an oil field brine solution of these reagents.

In many oil fields large volumes of water are produced and must be disposed of where water flooding operations are not in use or where water flooding operations cannot handle the amount of produced water. Most States have laws restricting pollution of streams and land with produced waters, and oil producers must then find some method of disposing of the waste produced salt water. In many instances therefore, the salt water is disposed of by injecting the water into permeable low pressure strata below the fresh water level. The formation into which the water is injected is not the oil producing formation and this type of disposal is defined as salt water disposal or waste water disposal. The problems of corrosion of equipment are analogous to those encountered in the secondary recovery operation by water flooding.

The compounds of this invention can also be used in such water disposal wells thus providing a simple and economical method of solving the corrosion problems encountered in disposing of unwanted water.

Water flood and waste disposal operations are too well known to require further elaboration. In essence, the flooding operation is effected in the conventional manner except that the flooding medium contains a minor amount of these compounds, sufficient to prevent corrosion.

While the flooding medium employed in accordance with the present invention contains water or oil field brine and the compounds of this invention, the medium may also contain other materials. For example, the flooding medium may also contain other agents such as surface active agents or detergents which aid in wetting throughout the system and also promote the desorption of residual oil from the formation, sequestering agents which prevent the deposition of calcium and/or magnesium compounds in the interstices of the formation, bactericides which prevent the formation from becoming plugged through bacterial growth, tracers, etc. Similarly, they may be employed in conjunction with any of the operating techniques commonly employed in water flooding and water disposal processes, for example five spot flooding, peripheral flooding, etc. and in conjunction with other secondary recovery methods.

The concentration of the corrosion inhibitors of this invention will vary widely depending on the particular compound, the particular system, etc. Concentration of at least about ¼ p.p.m., such as about ¼ to 7,500 p.p.m., for example about 1 to 5,000 p.p.m., advantageously about 10 to 1,000 p.p.m., but preferably about 15–250 p.p.m. may be employed. Larger amounts can also be employed such as 1.5–5.0% although these is generally no commercial advantage in so doing.

For example, since the success of a water flooding operation manifestly depends upon its total cost being less than the value of the additional oil recovered from the oil reservoir, it is quite important to use as little as possible of these compounds consistent with optimum corrosion inhibition. Since these compounds are themselves inexpensive and are used in low concentrations, they enhance the success of a flood operation by lowering the cost thereof.

By varying the constituents of the composition, the compounds of this invention can be made more oil or more water soluble, depending on whether the composition is to be employed in oil or water systems.

Although the manner of practicing the present invention is clear from the foregoing description, the following non-limiting specific examples are included for purposes of illustration.

CORROSION TESTS

The test procedure includes measurement of the corrosive action of fluids inhibited by the compositions herein upon sand-blasted SAE-1020 steel coupons under accelerating conditions.

In the test a container is charged with 20% (wt.) sulfuric acid, 0.25% of chemical and the acid solution heated to 190° F. Pre-weighted steel coupons are emerged in the acid solution for 15 minutes and the weight loss is determined. Percent protection is calculated from $$\frac{R_1 - R_2}{R_1} \times 100\%$$

where $R_1$ is corrosion rate of uninhibited fluids
where $R_2$ is corrosion rate of inhibited fluids.

The results are presented in the following Table where the inhibitor concentration in each example is 1000 p.p.m.

Table II

| Product from Example | % Protection |
|---|---|
| 1 | 58 |
| 2 | 63 |
| 4 | 88 |
| 9 | 75 |
| 12 | 75 |
| 13 | 82 |

The compositions of this invention were tested under actual oil field conditions to yield the results presented in the following table.

Table III

| Product from example | 50 p.p.m. | Time | mpy #1 | #2 | #3 |
|---|---|---|---|---|---|
| 1 | | 1 hr. | 55 | 16 | 1.2 |
| | | 2 hrs. | 50 | 4.2 | 0.9 |
| | | 3 hrs. | 52 | 1.3 | 0.8 |
| | | 5 hrs. | 50 | 1.3 | 1.0 |
| 12 | | 1 hr. | 44 | 1.6 | 0.8 |
| | | 2 hrs. | 42 | 0.5 | 0.5 |
| | | 3 hrs. | 42 | 0.5 | 0.5 |

1 Blank
2 Precorroded for 6 hrs., inhibited
3 Fresh, inhibited

The corrosion rate measurements in the above Table III were measured with an instrument for measurements of instantaneous corrosion rates of the type described in U.S. Pat. No. 3,406,101.

We claim:

1. A process of inhibiting the corrosion of metals which comprises treating a system, wherein metals are affected by corrosion, with a compound of the formula

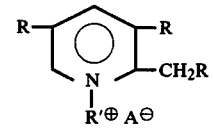

where R is an alkyl, hydroxyalkyl, cycloalkyl or heterocyclic group and R' is an alkyl, hydroxyalkyl, cycloalkyl, aryl or heterocyclic group, and A⊖ is a carboxylate anion.

2. The process of claim 1 where R is alkyl and R' is alkyl, hydroxyalkyl, cycloalkyl or aryl.

3. The process of claim 1 where R and R' are alkyl.

4. The process of claim 3 where A⊖ is acetate.

* * * * *